United States Patent [19]

Beihoffer et al.

[11] Patent Number: 5,763,658

[45] Date of Patent: Jun. 9, 1998

[54] METHOD FOR REMOVAL OF PHENOTHIAZINE INHIBITOR FROM ACRYLIC ACID

[75] Inventors: Thomas W. Beihoffer, Arlington Heights; Jerald W. Darlington, Marengo; David A. Eckert, Gurnee, all of Ill.

[73] Assignee: AMCOL International Corporation, Arlington Heights, Ill.

[21] Appl. No.: 544,881

[22] Filed: Oct. 18, 1995

[51] Int. Cl.$^6$ .................................................... C07C 51/42
[52] U.S. Cl. .................................................... 562/600
[58] Field of Search .................................................... 562/600

[56] References Cited

U.S. PATENT DOCUMENTS

| | | | |
|---|---|---|---|
| 1,402,112 | 1/1922 | Tellier. | |
| 1,408,655 | 3/1922 | Stratford. | |
| 1,408,656 | 3/1922 | Stratford. | |
| 1,524,843 | 2/1925 | Ruprecht. | |
| 1,544,210 | 6/1925 | Bierce. | |
| 1,731,702 | 10/1929 | Black. | |
| 1,739,734 | 12/1929 | Raine et al.. | |
| 2,470,872 | 5/1949 | Secor | 252/450 |
| 2,836,615 | 5/1958 | Heininger et al. | 260/465.9 |
| 4,021,310 | 5/1977 | Shimizu et al. | 203/8 |
| 4,187,382 | 2/1980 | Cowherd, III et al. | 560/185 |
| 4,832,793 | 5/1989 | Alexander | 162/181.8 |
| 4,919,818 | 4/1990 | Alexander | 210/660 |

FOREIGN PATENT DOCUMENTS

| | | |
|---|---|---|
| 600 453 | 4/1948 | United Kingdom. |
| 600453 | 4/1948 | United Kingdom. |

Primary Examiner—Gary Geist
Assistant Examiner—Rosalynd Keys
Attorney, Agent, or Firm—Marshall, O'Toole, Gerstein, Murray & Borun

[57] ABSTRACT

A process for decreasing the concentration of phenothiazine from a solution of acrylic acid by contacting the acrylic acid solution with a hydrophobic clay, such as an organophilic clay; or by protonating the phenothiazine, oxidizing the phenothiazine, and contacting the protonated, oxidized phenothiazine with a hydrophilic clay, such as an acid-activated smectite clay or sodium bentonite clay to sorb (absorb and/or adsorb) the phenothiazine into or onto the clay. Once sorbed onto the smectite clay, the phenothiazine easily can be removed, together with the clay, from the solution of acrylic acid, e.g., by filtration.

20 Claims, 1 Drawing Sheet

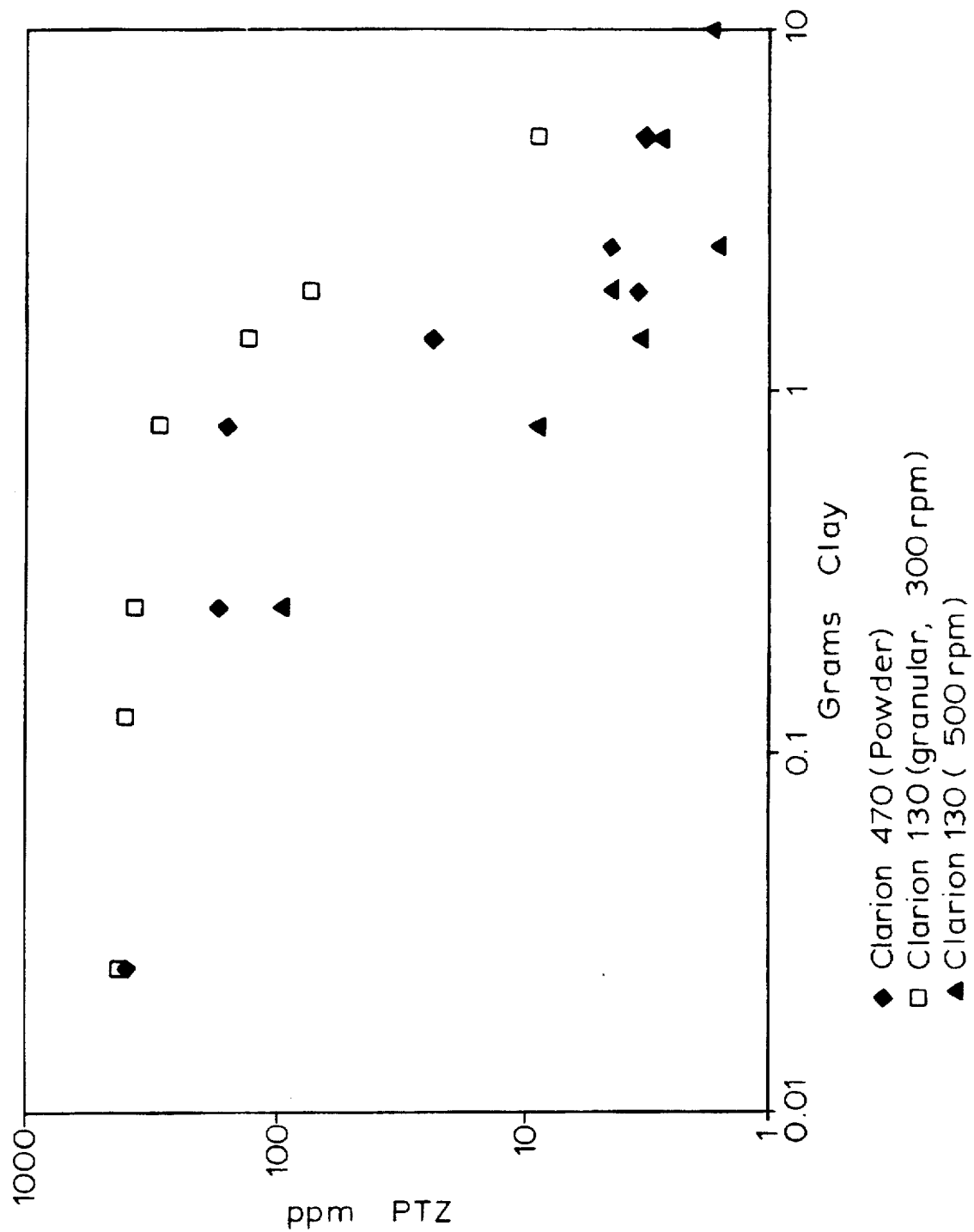

5,763,658

1

METHOD FOR REMOVAL OF PHENOTHIAZINE INHIBITOR FROM ACRYLIC ACID

FIELD OF THE INVENTION

The present invention is directed to a method for removing a phenothiazine (PTZ) polymerization inhibitor from a solution of phenothiazine and acrylic acid. More particularly, the present invention is directed to a method of removing a substantial proportion of phenothiazine, in a concentration above 100 parts per million (PPM), from acrylic acid, by contacting the phenothiazine-containing acrylic acid with a hydrophobic smectite clay, e.g., an organophilic clay; or with a hydrophilic clay together with a protonating agent for phenothiazine, e.g., a mineral acid, and an oxidizing agent for phenothiazine, e.g., sodium persulfate, hydrogen peroxide, and/or ceric ammonium nitrate to reduce the phenothiazine concentration to below 100 PPM, preferably below 10 PPM, more preferably below 5 PPM, and most preferably below 1 PPM.

BACKGROUND OF THE INVENTION

Acrylic acid is stabilized against premature polymerization by the addition of chemical compounds that interfere with free radical formation. These compounds (inhibitors) generally consist of two types: (1) storage/transport inhibitors, and (2) process inhibitors.

The storage/transport inhibitors generally are compounds that work in conjunction with oxygen to inhibit polymerization. These inhibitors are designed to prevent polymerization during transport and storage, yet the polymerization inhibiting property can be overcome to allow polymerization to occur, when desired, without having to remove the inhibitor. An example of such an inhibitor is the methyl ether of hydroquinone, which is present in most high-quality acrylic acid at a concentration of approximately 200 PPM. In most commercial acrylic acid polymerization processes, the methyl ether of hydroquinone remains in the system and is overcome by the reduction in oxygen content of the system along with the addition of a sufficient amount of free radical initiators to quickly overpower the inhibitor.

Process inhibitors are compounds that are used to prevent polymerization under the extreme conditions that are often present during the manufacture of monomers. These inhibitors must be effective without the presence of oxygen and at high temperatures that are encountered while distilling monomers at high temperatures (>100° C.). An example of such an inhibitor is phenothiazine. Phenothiazine is used during the manufacture of acrylic acid and a substantial proportion of the phenothiazine must be removed, to levels below about 10 PPM, preferably below about 1 PPM, prior to polymerization due to its strong polymerization inhibition effects. The industry specification for polymerization grade acrylic acid requires that phenothiazine concentration be less than 1 PPM.

The removal of phenothiazine from acrylic acid requires a sophisticated purification step (usually distillation and crystallization) that can reduce the phenothiazine level from approximately 500 PPM to essentially free of phenothiazine (less than 1 PPM). The phenothiazine-free acrylic acid then must be re-inhibited, e.g., with the methyl ether of hydroquinone, to allow safe transport and storage.

The use of methyl ether of hydroquinone as an inhibitor imposes limitations on the time, distance and conditions under which acrylic acid can be transported and stored. Acrylic acid manufacturers have indicated that methyl ether

2 of hydroquinone is not suitable as an inhibitor for extremely long delivery times, such as would occur when shipping acrylic acid from Europe to the United States aboard a ship. As a result, most factories that use acrylic acid need to be located relatively near an acrylic acid manufacturing facility (usually within one week delivery time).

Phenothiazine-inhibited acrylic acid does not have the transport and storage limitations characteristic of methyl ether of hydroquinone-inhibited acrylic acid. Acrylic acid is routinely shipped all over the world when inhibited with phenothiazine. The disadvantage of this is that the acrylic acid still requires the final purification, e.g., expensive distillation and crystallization steps, to remove the phenothiazine and subsequent re-inhibition with methyl ether of hydroquinone to make it suitable for use in polymerization processes.

The present invention is directed to a simple process that allows the removal of phenothiazine from acrylic acid. This process will allow more flexibility in the shipment/storage of acrylic acid and allows the production of quality polymer products from inexpensive, low-grade acrylic acid that has not undergone a final purification step to remove phenothiazine.

SUMMARY OF THE INVENTION

In brief, the present invention is directed to a process for decreasing the concentration of phenothiazine from a solution of acrylic acid by contacting the acrylic acid solution with a hydrophobic clay, such as an organophilic clay; or by protonating the phenothiazine, oxidizing the phenothiazine, and contacting the protonated, oxidized phenothiazine with a hydrophilic clay, such as an acid-activated smectite clay or sodium bentonite clay to sorb (absorb and/or adsorb) the phenothiazine into or onto the clay. Once sorbed onto the smectite clay, the phenothiazine easily can be removed, together with the clay, from the solution of acrylic acid, e.g., by filtration. In the preferred method, the phenothiazine-containing acrylic acid is contacted with the hydrophilic clay, e.g., an acid-activated smectite clay or a sodium bentonite clay in the presence of a compound capable of protonating the phenothiazine, e.g., a mineral acid, such as $H_2SO_4$, HCl, $HNO_3$, and the like, and in the presence of a compound capable of oxidizing the phenothiazine, e.g., sodium persulfate, hydrogen peroxide, or ceric ammonium nitrate so that protonation, oxidation, and sorption can be carried out in a single step. In accordance with a preferred embodiment, to achieve maximum removal of phenothiazine, the acrylic acid solution again is contacted with an acid-activated smectite clay or a sodium bentonite clay in a second process step, with or without additional phenothiazine protonation and oxidation compounds, to achieve essentially complete removal of phenothiazine (to a level in the range of 0–1 PPM).

It is theorized that protonation ($H^+$) and oxidation (O) of phenothiazine result in the formation of the following cationic molecules A and B that are securely sorbed by smectite clays by ion exchange in place of a metal cation, e.g., $Mg^+$, $Na^+$, $Ca^+$, $Li^+$ and the like, particularly $Na^+$ and $Ca^+$, so that the phenothiazine-sorbed clay easily can be separated from the acrylic acid solution, e.g., by filtration, to remove the phenothiazine from the acrylic acid solution.

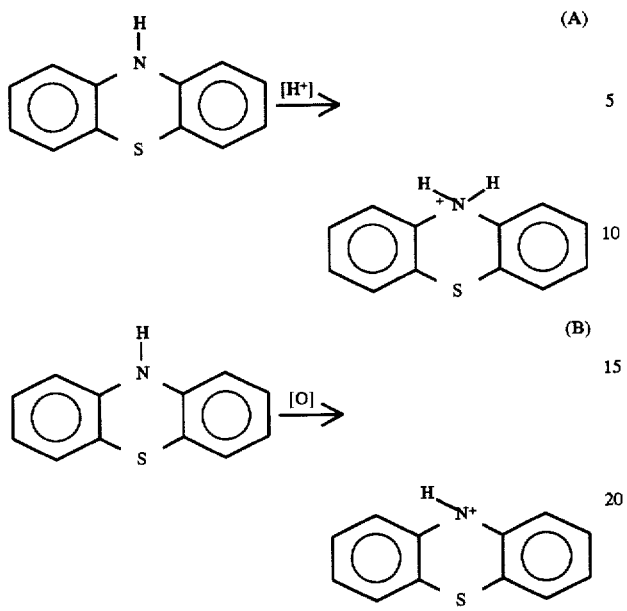

Accordingly, one aspect of the present invention is to provide an efficient method for reducing the concentration of phenothiazine in a solution of acrylic acid.

Another aspect of the present invention is to provide a method of removing phenothiazine from acrylic acid in a process that requires little capital investment so that the process can be installed and used by each acrylic acid end user. In this manner, phenothiazine can be incorporated in sufficient quantities in acrylic acid for long shipment and storage times, without unintended polymerization, and when the acrylic acid is needed, it can be processed in accordance with the present invention, easily and inexpensively for essentially complete removal of the phenothiazine polymerization inhibitor.

Still other aspects of the present invention are to increase the safety of transporting and storage of high purity glacial acrylic acid. As discussed above, high purity glacial acrylic acid is prone to undesired polymerization during the storage and transportation phases. This invention allows a manufacturer of high purity glacial acrylic acid to add a small amount (e.g. 10–20 PPM) of phenothiazine to the high purity glacial acrylic acid to ensure stability of the acrylic acid during storage and transportation. This invention provides the end user with a method to remove the phenothiazine in order to polymerize the acrylic acid.

The above and other aspects and advantages of the present invention will become more apparent from the following detailed description of the preferred embodiments of the invention taken in conjunction with the drawing.

BRIEF DESCRIPTION OF THE DRAWING

The FIGURE is a graph of phenothiazine isotherms for a number of acid-activated clay treatments, the clays having various particle sizes.

DETAILED DESCRIPTION OF THE PREFERRED EMBODIMENTS

The process of the present invention purifies phenothiazine-inhibited acrylic acid to allow a lower-grade acrylic acid to be used to produce useful products, such as cross-linked polyacrylate superabsorbent polymers. This procedure, while documented here with a slurry process and clay adsorbents, should be adaptable to other processes that expose acrylic acid to an adsorbent, and to other monomers that may contain a phenothiazine polymerization inhibitor.

It has been found that phenothiazine can be removed from acrylic acid by exposing the inhibited acrylic acid to certain solid adsorbents. The adsorbent will remove the inhibitor from acrylic acid, yielding a purified acrylic acid that can be used as-is to make polymers, or can be re-inhibited with a different, e.g., less effective, shorter life inhibitor, such that the inhibited acrylic acid composition can be polymerized while containing the different inhibitor in a variety of polymerization processes. The most preferred adsorbent for this invention is an acid-washed (acid-activated) smectite clay, such as the acid-activated clays disclosed in U.S. Pat. Nos. 1,402,112; 1,408,655; 1,408,656; 1,524,843; 1,544,210; 1,731,702; 1,739,734; 2,470,872; 4,832,793; and 4,919,818, hereby incorporated by reference.

In accordance with one embodiment of the present invention, the invention includes the discovery that by chemically treating the phenothiazine-inhibited acrylic acid with a PTZ protonating agent and a PTZ oxidizing agent, the ability to sorb the phenothiazine onto adsorbents, particularly a hydrophilic smectite clay, is significantly improved. In another embodiment, it has been found that the PTZ is adequately removed by contact with a hydrophobic clay, particularly an organophilic smectite clay, without protonating or oxidizing agents for the PTZ.

EXPERIMENTAL

Examples 1 and 2 are directed to the removal of phenothiazine from acrylic acid by contact with a hydrophilic smectite clay, particularly an acid-activated smectite (calcium bentonite) clay, or sodium bentonite clay; a PTZ protonating agent; and a PTZ oxidizing agent.

Example 1

To a 100 mL disposable beaker, add 50 g of phenothiazine-containing acrylic acid and 0.15 g of 10% $H_2SO_4$; stir at 500 rpm for 5 minutes using a stir bar (1×⅝") and a magnetic stir plate (room temperature). Add 0.65 g of 1% $Na_2S_2O_8$; stir 5 minutes. Add 2.5 g acid-activated smectite clay (CLARION 470 of AMCOL International Corporation) and continue stirring for 30 minutes. Filter using 15 cm Whatman 41 filter paper. Analyze according to phenothiazine test method.

Example 2

To a 200 ml beaker add 50 g of PTZ-containing acrylic acid, 50 g of de-ionized water and 0.1 g of 40% $H_2SO_4$; stir at 500 PPM for 5 minutes. Add 0.4 g 4% $Na_2S_2O_8$ and stir for 5 minutes. Add 5 g acid-activated smectite clay (CLARION 470 of AMCOL International Corporation) and continue stirring for 30 minutes. Filter using 15 cm Whatman 41 filter paper. Analyze according to PTZ test method. PTZ concentration reduced from ~350 PPM to about 5 PPM.

Several different adsorbents and chemical treatment procedures were tried to determine the most effective process for removing phenothiazine from crude acrylic acid. Table I shows the results of the direct exposure of phenothiazine-inhibited acrylic acid to various adsorbents, using no chemical pretreatment.

Examples 3–5 illustrate the removal of phenothiazine from acrylic acid by contact with a hydrophobic smectite clay, without a PTZ protonating agent or a PTZ oxidizing agent.

Examples 3-5

To a 200 ml beaker add 50 g of PTZ-containing acrylic acid, 50 g of de-ionized water, and 10 g of hydrophobic (organophilic) clay (CLARION PM 100). Stir at 500 PPM for 30 minutes. Filter using 15 cm Whatman 41 filter paper. Analyze according to PTZ test method. PTZ concentration reduced from ~350 PPM to 75 PPM.

Example 3 was repeated, in Examples 4 and 5, on the same PTZ-containing acrylic acid using lower amounts of organophilic clay with the following results for Examples 3-5:

| Example | Sorbent | Grams of Sorbent/100 g Acrylic Acid | Mixing Time, Min. | Phenothiazine Concentration; PPM |
|---|---|---|---|---|
| 3 | hydrophobic (organophilic)* clay | 20 | 30 | ≅5 |
| 4 | hydrophobic (organophilic)* clay | 10 | 30 | ≅25 |
| 5 | hydrophobic (organophilic)* clay | 5 | 30 | ≅100 |

*Sodium montmorillonite reacted with a dimethyl ditallow quaternary ammonium ion to make the clay organophilic (CLARION PM 100 from AMCOL International Corporation).

TABLE I

| Sorbent | Grams of Sorbent/100 g Acrylic Acid | Mixing Time, Min. | Phenothiazine Concentration; PPM |
|---|---|---|---|
| None | 0 | 0 | 370 |
| DOWEX (ion exchange resin) | 2 | 30 | 252 |
| DARCO (FGD) (act. carbon) | 5 | 120 | 219 |
| NORIT SX1 (act. carbon) | 5 | 120 | 143 |
| DARCO KB (act. carbon) | 5 | 134 | 134 |
| CLARION 470 (acid-activated smectite clay) | 5 | 30 | 248 |

The results of Table I show that all the sorbents exhibit the ability to reduce the phenothiazine level in the acrylic acid but that only the methods of the present invention reduce the PTZ to a level that is required by industry specifications to allow the acrylic acid to be used in polymerization reactions.

Table II shows how the composition and process of the present invention provide for the near total removal of phenothiazine from acrylic acid. When the phenothiazine-inhibited acrylic acid is treated with a phenothiazine protonator, e.g., sulfuric acid, and a phenothiazine oxidizing agent, e.g., sodium persulfate, prior to exposure to the sorbent, the efficiency of the sorbent is greatly improved. In the case of acid-activated calcium bentonite clay (CLARION 470) (an acid-washed smectite clay) two clay treatments can reduce the phenothiazine level to below 1 PPM.

TABLE II

| Sorbent | Grams of Sorbent/100 g Acrylic Acid | Chemical Treatment* | Mixing time, Min. | Phenothiazine; PPM |
|---|---|---|---|---|
| None | 0 | None | 0 | 370 |
| Acid-Activated Calcium Bentonite | 5 | 0 | 30 | 248 |
| Acid-Activated Calcium Bentonite | 5 | H | 30 | 123 |
| Acid-Activated Calcium Bentonite | 5 | H + N | 30 | 57 |
| Acid-Activated Calcium Bentonite | 5 | 2H + 2N | 30 | 8 |
| Acid-Activated Calcium Bentonite | 5 | H + 2N | 30 | 3 |
| Acid-Activated Calcium Bentonite | 5 | 2H + N | 30 | 5 |
| NORIT SX1 | 5 | 1H + 2N | 30 | 74 |
| DARCO KB | 5 | 1H + 2N | 30 | 69 |
| Acid-Activated Calcium Bentonite | 5 then 1 | 2H + 2N | 30 then 30 | 0 |
| DOWEX | 2 | N | 30 | 182 |

*Chemical treatment H = 0.1 gram Conc. $H_2SO_4$ per 100 grams of clay; N = 0.1 gram 10% $Na_2S_2O_8$ per 100 grams of clay.

Further evidence of the utility of the invention can be seen from the adsorption isotherms generated by two different clay samples in FIG. 1.

The isotherms for CLARION 470 and 130 (both acid-activated calcium bentonite clays) show that the phenothiazine reduction is a function of smectite clay treatment and can be controlled to produce acrylic acid with a low phenothiazine level.

Polymerization of Treated Acrylic Acid

Table III shows how the compositions and methods of the present invention can be used to prepare polymerization grade acrylic acid from acrylic acid that is inhibited with approximately 250 PPM phenothiazine (crude acrylic acid). The data in Table III show the results from the polymerization of (a) untreated (crude) phenothiazine-containing acrylic acid, (b) treated acrylic acid, and (c) standard polymerization-grade acrylic acid (HM grade acrylic acid from BASF). The treatment was H+N+5% CLARION 470 followed by a second treatment with 1% by weight acid-activated smectite clay (CLARION 470) (see Table II). The polymerizations (A and B) converted the acrylic acid into superabsorbant polymers and the Table gives the performance of the polymers, including gel volume (GV), absorption underload (AUL) and extractables (EXT).

TABLE III

| Polymer | Acrylic Acid | Phenothiazine PPM | GV g/g | AUL g/g | EXT |
|---|---|---|---|---|---|
| A | Crude Acrylic Acid | 250 | No Polymer Formed | | |
| A | Crude Acrylic Acid Treated by Acid-Activated Smectite | <5 | 32.9 | 30.3 | 2.9 |
| A | HM Grade Acrylic Acid | <1 | 37.6 | 31.8 | 6.2 |
| B | Crude Acrylic Acid | 250 | No Polymer Formed | | |
| B | Crude Acrylic Acid | <5 | 33.7 | 29.9 | 5.3 |

TABLE III-continued

| Polymer | Acrylic Acid | Phenothiazine PPM | GV g/g | AUL g/g | EXT |
|---|---|---|---|---|---|
| | Treated by Acid-Activated Smectite | | | | |
| B | HM Grade Acrylic Acid | <1 | 37.7 | 32.7 | 2.8 |
| C | Crude Acrylic Acid | 350 | No Polymer Formed | | |
| C | Crude Acrylic Acid Treated by Sodium Bentonite | <5 | 35.1 | 30.1 | 4.4 |
| C | Crude Acrylic Acid Treated by Sodium Bentonite | <5 | 35.6 | 29.1 | 5.2 |

The results show that the treatment process of the present invention allows crude acrylic acid to be polymerized into a superabsorbent polymer with properties approaching that of commercial polymerization grade acrylic acid. Without treatment, the polymerization reaction will not occur.

Methyl Ether of Hydroquinone

High purity polymerization grades of acrylic acid are inhibited with methyl ether of hydroquinone. Methyl ether of hydroquinone provides sufficient inhibition to prevent polymerization at low temperatures and does not interfere with polymerization when "overpowered" with initiators during synthesis. It may be necessary to re-inhibit treated phenothiazine-inhibited acrylic acid with methyl ether of hydroquinone to prevent polymerization during storage. It would be convenient if the methyl ether of hydroquinone could be added to the acrylic acid prior to treatment and, if the methyl ether of hydroquinone is not effected or adsorbed during the treatment process, would remain in the crude acrylic acid after treatment to provide inhibition after phenothiazine removal.

Testing has found that a significant percentage of methyl ether of hydroquinone remains in the acrylic acid after the treatment process (Table IV). This implies that it may be possible to "exchange" phenothiazine for methyl ether of hydroquinone by pretreating the crude acrylic acid with methyl ether of hydroquinone prior to the phenothiazine removal process of the present invention.

TABLE IV

| Treatment | Residual Methyl Ether Hydroquinone, PPM |
|---|---|
| None | 256 |
| 5% CLARION 130*/5% CLARION 130*/5% CLARION 130* | 256 |
| H + N + 5% CLARION 130* | 155 |
| H + N + 5% CLARION 130*/5% CLARION 130*/5% CLARION 130* | 199 |
| H + N + 5% CLARION 130*/H + N + 5% CLARION 130*/5% CLARION 130* | 97 |
| H + N + 5% CLARION 130*/H + N + 5% CLARION 130*/H + N + 5% CLARION 130* | 56 |
| Hydrophobic (organophilic) Clay (CLARION PM 100) | 202 |
| Sodium Bentonite | 194 |
| H + Sodium Bentonite | 212 |
| N + Sodium Bentonite | 178 |
| H + N + Sodium Bentonite | 192 |

*CLARION 130 is an acid-activated calcium bentonite clay - the calcium bentonite being mined in Oklahoma.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the processes may be varied substantially without departing from the spirit of the invention, and the exclusive use of all modifications which come within the scope of the appended claims is reserved.

What is claimed is:

1. A method for removing a phenothiazine polymerization inhibitor from a solution of acrylic acid containing more than 100 PPM phenothiazine, comprising:

contacting the acrylic acid solution with a hydrophobic smectite clay in an amount sufficient to reduce the concentration of phenothiazine to below 100 PPM.

2. A method for removing a phenothiazine polymerization inhibitor from a solution of acrylic acid containing more than 100 PPM phenothiazine, comprising:

protonating the phenothiazine; and oxidizing the phenothiazine, simultaneous with or prior to contacting the acrylic acid solution with a hydrophilic smectite clay.

3. The method of claim 1, wherein the hydrophobic smectite clay is an organophilic smectite clay.

4. The method of claim 2, wherein the smectite clay is an acid-activated smectite clay.

5. The method of claim 2, wherein the smectite clay is sodium bentonite clay.

6. The method of claim 1, wherein the concentration of phenothiazine is reduced to below 5 PPM.

7. The method of claim 2, wherein the concentration of phenothiazine is reduced to below 5 PPM.

8. The method of claim 7, wherein the concentration of phenothiazine is reduced to below 1 PPM.

9. The method of claim 6, further including a second step of contacting the acrylic acid solution with a hydrophilic smectite clay.

10. The method of claim 2, wherein the phenothiazine is protonated by adding a mineral acid to the phenothiazine-containing solution of acrylic acid.

11. The method of claim 2, wherein the phenothiazine is oxidized by adding an oxidizing agent to the phenothiazine-containing solution of acrylic acid.

12. The method of claim 10, wherein the mineral acid is selected from the group consisting of sulfuric acid, hydrochloric acid, nitric acid, and mixtures thereof.

13. The method of claim 11, wherein the oxidizing agent is selected from the group consisting of sodium persulfate, hydrogen peroxide, cerric ammonium nitrate, and mixtures thereof.

14. The method of claim 1, wherein the acrylic acid solution is contacted with the smectite clay by adding the smectite clay to the phenothiazine-containing acrylic acid solution.

15. The method of claim 14, further including the step of separating the acrylic acid solution from the smectite clay, thereby removing phenothiazine adsorbed by the smectite clay.

16. The method of claim 2, wherein the smectite clay is selected from the group consisting of calcium bentonite clay, sodium bentonite clay, and mixtures thereof.

17. The method of claim 16, further including the step of separating the acrylic acid solution from the smectite clay, thereby removing phenothiazine adsorbed by the smectite clay.

18. The method of claim 3, wherein the organophilic clay is a calcium bentonite reacted with a dimethyl ditallow quaternary ammonium ion.

19. The method of claim 1 further including the step of contacting the phenothiazine-containing acrylic acid with a methyl ether of hydroquinone prior to contact of the acrylic acid with the hydrophobic smectite clay.

20. The method of claim 2 further including the step of contacting the phenothiazine-containing acrylic acid with a methyl ether of hydroquinone prior to contact of the acrylic acid with the hydrophilic smectite clay.

* * * * *